(12) United States Patent
Ferren

(10) Patent No.: US 9,170,214 B2
(45) Date of Patent: Oct. 27, 2015

(54) MOTION-BASED RADIOGRAPH INTERLOCK SYSTEMS, STRUCTURES, AND PROCESSES

(75) Inventor: Bran Ferren, Beverly Hills, CA (US)

(73) Assignee: APPLIED MINDS, LLC, Burbank, CA (US)

( * ) Notice: Subject to any disclaimer, the term of this patent is extended or adjusted under 35 U.S.C. 154(b) by 247 days.

(21) Appl. No.: 13/612,378

(22) Filed: Sep. 12, 2012

(65) Prior Publication Data

US 2013/0064346 A1 Mar. 14, 2013

Related U.S. Application Data

(60) Provisional application No. 61/534,239, filed on Sep. 13, 2011.

(51) Int. Cl.
*A61B 6/14* (2006.01)
*G01N 23/04* (2006.01)
*A61B 6/00* (2006.01)

(52) U.S. Cl.
CPC *G01N 23/04* (2013.01); *A61B 6/14* (2013.01); *A61B 6/547* (2013.01); *A61B 6/4452* (2013.01); *G01N 2223/612* (2013.01)

(58) Field of Classification Search
CPC ...... A61B 6/5264; A61B 6/527; A61B 6/542; A61B 6/586; A61B 6/587; A61B 6/4452; A61B 6/4476; A61B 2017/00694; A61B 6/14; A61B 6/032; A61B 6/541; A61B 6/547; A61B 19/5244; G01N 29/26; G01N 23/04; H05G 1/62; H05G 1/56
USPC ............ 378/8, 38, 62, 95, 114, 115, 116, 207
See application file for complete search history.

(56) References Cited

U.S. PATENT DOCUMENTS

| | | | | |
|---|---|---|---|---|
| 5,033,070 A * | 7/1991 | Kanerva et al. | .................. | 378/39 |
| 5,870,450 A * | 2/1999 | Khutoryansky et al. | ...... | 378/197 |
| 6,461,040 B1 * | 10/2002 | Mattson et al. | ............... | 378/205 |
| 7,559,693 B2 * | 7/2009 | Sonani | .......................... | 378/206 |
| 8,275,093 B2 * | 9/2012 | Rothschild | ...................... | 378/62 |
| 2005/0001112 A1 * | 1/2005 | Hubner et al. | ................ | 248/121 |
| 2005/0027194 A1 * | 2/2005 | Adler et al. | ................... | 600/427 |
| 2008/0273659 A1 * | 11/2008 | Guertin et al. | .................. | 378/65 |

OTHER PUBLICATIONS

Ron Jenkins, X-ray Techniques: Overview, 2000, John Wiley & Sons Ltd, p. 3.*

* cited by examiner

*Primary Examiner* — David J Makiya
*Assistant Examiner* — Julio M Duarte-Carvajalino
(74) *Attorney, Agent, or Firm* — Michael A. Glenn; Perkins Coie LLP

(57) ABSTRACT

A motion-based interlock apparatus, system, and method prevent an x-ray source in an x-ray machine from activating if the current relative motion between the x-ray source and an image receptor would compromise the quality of the resulting plain radiograph. The system activates the interlock based on either or both of the velocity and acceleration of the tubehead, as measured by instrumentation corresponding to any of the tubehead, the extension arm, or off board the x-ray machine. The system may preferably compare the measured motion against one or more acceptable motion thresholds. If the measured motion exceeds one or more of the acceptable motion thresholds, exposure may preferably be delayed until the motion of the tubehead subsides. By ensuring that the image is not exposed while the tubehead is moving substantially, the quality of the resultant radiograph is improved.

25 Claims, 10 Drawing Sheets

MOTION-BASED RADIOGRAPH INTERLOCK SYSTEMS, STRUCTURES, AND PROCESSES

CROSS REFERENCE TO RELATED APPLICATION AND CLAIM FOR PRIORITY

This Application claims priority to U.S. Provisional Patent Application No. 61/534,239, entitled Motion-Based Radiograph Interlock, filed 13 Sep. 2011, which is incorporated herein in its entirety by this reference thereto.

FIELD OF THE INVENTION

The present invention relates generally to the field of imaging systems and associated processes. More particularly, the present invention relates to x-ray radiograph systems, structures, and processes, such as for but not limited to dental and medical applications.

BACKGROUND OF THE INVENTION

Despite continuing advances in imaging technology, plain (projection) x-ray radiographs remain a staple diagnostic technology within the world of medicine. While magnetic resonance imaging (MRI) and computer tomography scans (CT scans) can reveal a wider range of tissue structures and better resolve spatial relationships, e.g. through three-dimensional or cross-sectional images, the relatively low cost, wide availability, and simplicity of plain radiographs make them the imaging technique of choice whenever possible.

In particular, plain radiographs remain in wide use in the field of dentistry. To obtain a radiograph, a dental technician positions an x-ray source and an image receptor on either side of the portion of the patient's palate to be imaged. Often, the image receptor is positioned intraorally, and is held in place against the patient's palate by the biting action of the patient on a bite plate or bite stick. For film-screen plain radiographs, the image receptor comprises an unexposed sheet of film that is exposed by incident x-ray radiation. For digital plain radiographs, which are becoming increasingly common, the image receptor comprises a sensor plate that converts incident x-ray radiation into digital information. In either case, the x-rays emitted from the x-ray source are partially blocked by dense tissues such as bone. The patient's teeth thus cast "shadows" on the image receptor. In the resulting image, either a developed film image or a digital image, bone structures appear as lighter regions among darker regions of softer tissue.

FIG. 1 shows an exemplary conventional dental x-ray machine 10, which typically comprises a base 12, an articulated extension arm 16, and a tubehead 20 housing an x-ray source. The base 12 anchors the x-ray machine 10 to the floor FLR of dental facility, and is typically accompanied by a control panel 26 with which a dental technician can adjust the radiograph parameters, and initiate image acquisition. In many instances, the control panel 26, or a second, auxiliary control panel, is removed from the base 12, e.g. outside the patient room, allowing the dental technician to initiate image acquisition from a location with reduced radiation exposure. The articulated extension arm 16 extends outward from the base 12 and supports the tubehead 20, allowing the tubehead 20 to be easily positioned and oriented as needed. The tubehead 20 typically comprises a heavy, e.g. lead, metal housing 22 that encloses the x-ray source, such as a hot cathode, i.e. Coolidge, x-ray tube.

The x-rays emitted by the x-ray tube emerge from the metal housing 22 through a lead collimator that partially collimates the x-ray beam. A tubehead seal, such as comprising a thin aluminum sheet, spans the lead collimator, to filter the long wavelength, low energy, i.e. soft, x-rays emitted by the x-ray tube and "harden" the x-ray beam 32. Soft x-rays do not effectively penetrate biological tissues but are instead absorbed. While soft x-rays are not useful for imaging, they remain potentially harmful, and are therefore typically filtered.

A position indicating device 24, typically comprising a lead-lined cylinder, extends outwards from the metal housing 22, coaxial with the x-ray beam, to further collimate the x-ray beam and assist the dental technician in aiming the x-ray beam.

Obtaining quality radiographs of patient's teeth is an important function of any dental technician. Indeed, poor quality radiographs, i.e. radiographs with poor resolution, makes detection of many adverse dental conditions, e.g. small, incipient fractures within a tooth, difficult or impossible. Relative motion of the tubehead 20, palate, and image receptor can lead to blurred features within a resulting radiograph. Accordingly, a dental technician will often instruct a patient to "Hold still!", while the technician exits the room and activates the x-ray tube to expose the radiograph.

Movement of the tubehead 20 is often detrimental to the quality of the exposed image. Despite the relatively rigid construction of the extension arm 16, the tubehead 20 often is exhibits substantial oscillatory movement after a dental technician positions it. The motion can persist while the dental technician exits the room to activate the x-ray tube, significantly compromising image quality. The partially collimated nature of the x-ray beam and, in the case of intraoral radiographs, the relatively small spatial separation between the palate and the image receptor mitigate the effects of such relative motion. Nonetheless, motion of the tubehead 20 can potentially degrade the quality of radiograph.

It would thus be advantageous to provide a structure, system, and/or process by which activation of an x-ray system is allowed to proceed under conditions wherein relative movement between a tubehead and the image receptor is acceptable. Such a structure, system, and/or process would provide a substantial technical advance.

Furthermore, it would be advantageous to provide a structure, system and/or process for preventing activation of an x-ray source if relative movement between a tubehead and the image receptor would otherwise result in poor quality x-ray images. Such a structure, system, and/or process would provide an additional technical advance.

SUMMARY OF THE INVENTION

A motion-based interlock apparatus, system, and method prevent an x-ray source in an x-ray machine from activating if the current relative motion between the x-ray source and an image receptor would compromise the quality of the resulting plain radiograph. The system activates the interlock based on either or both of the velocity and acceleration of the tubehead, as measured by instrumentation corresponding to any of the tubehead, the extension arm, or off board the x-ray machine. The system may preferably compare the measured motion against one or more acceptable motion thresholds. If the measured motion exceeds one or more of the acceptable motion thresholds, exposure may preferably be delayed until the motion of the tubehead subsides. By ensuring that the image is not exposed while the tubehead is moving substantially, the quality of the resultant radiograph is improved.

DETAILED DESCRIPTION OF PREFERRED EMBODIMENTS

Figure 1:
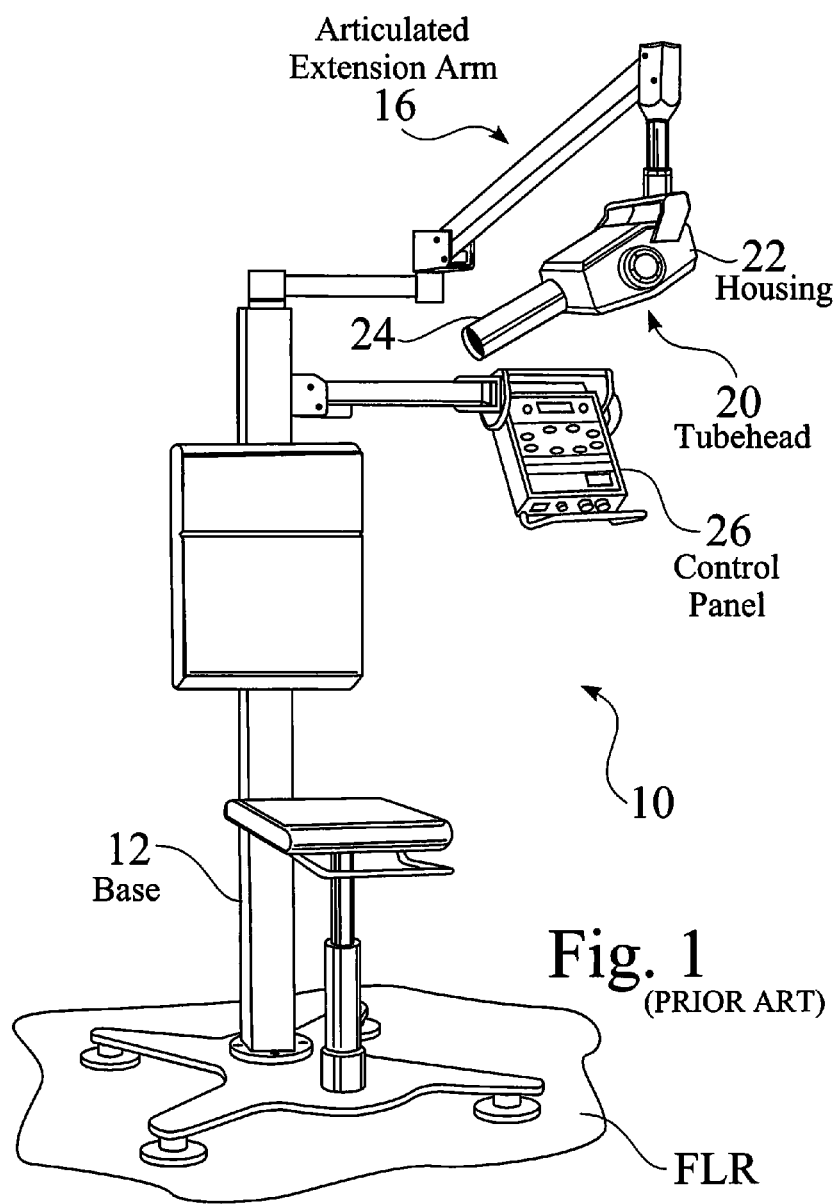
FIG. 1 is an exemplary view of a conventional dental x-ray machine.
Figure 2:
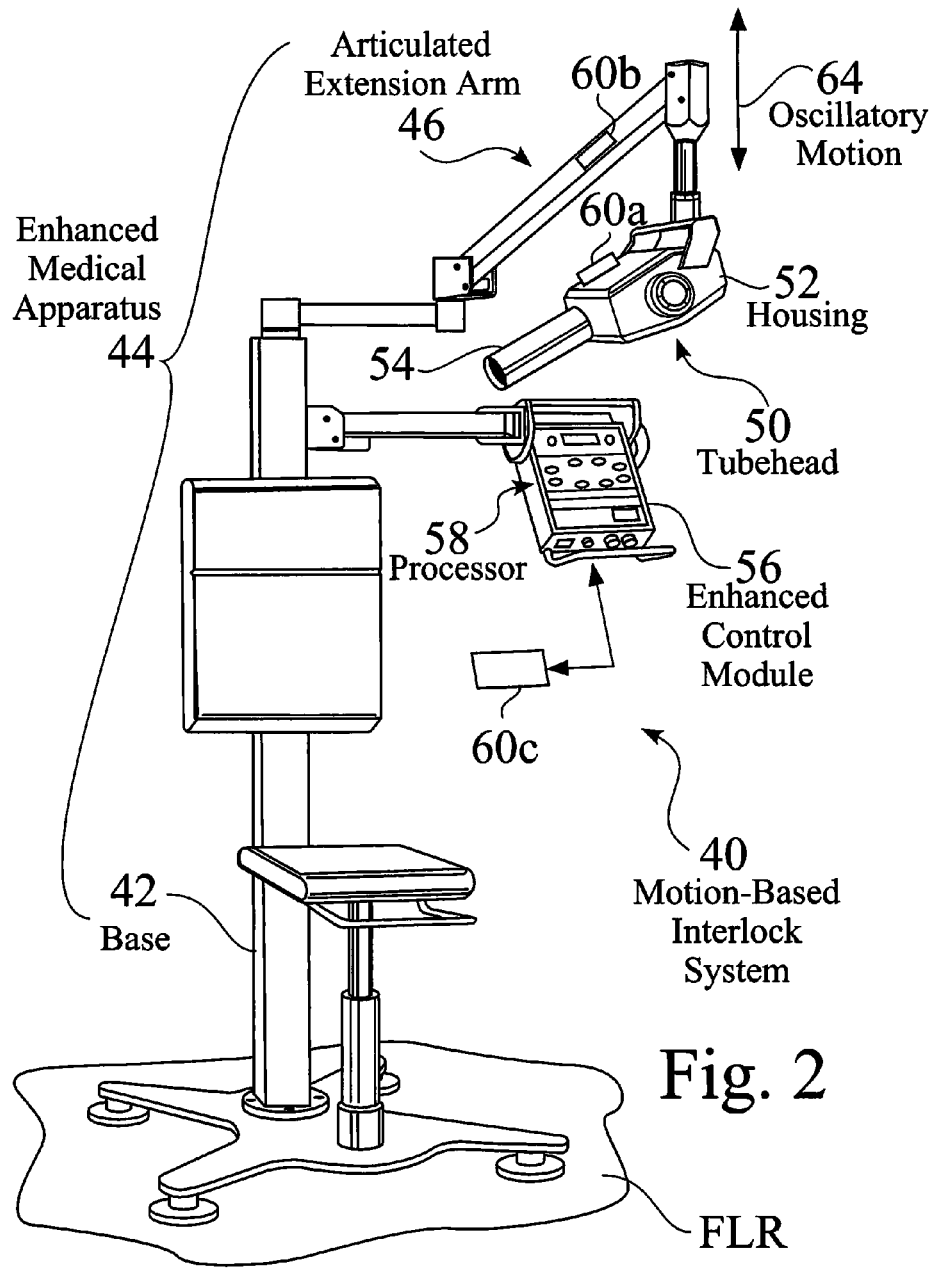
FIG. 2 is a schematic view of an exemplary enhanced medical apparatus having an integrated motion-based interlock system.
Figure 3:
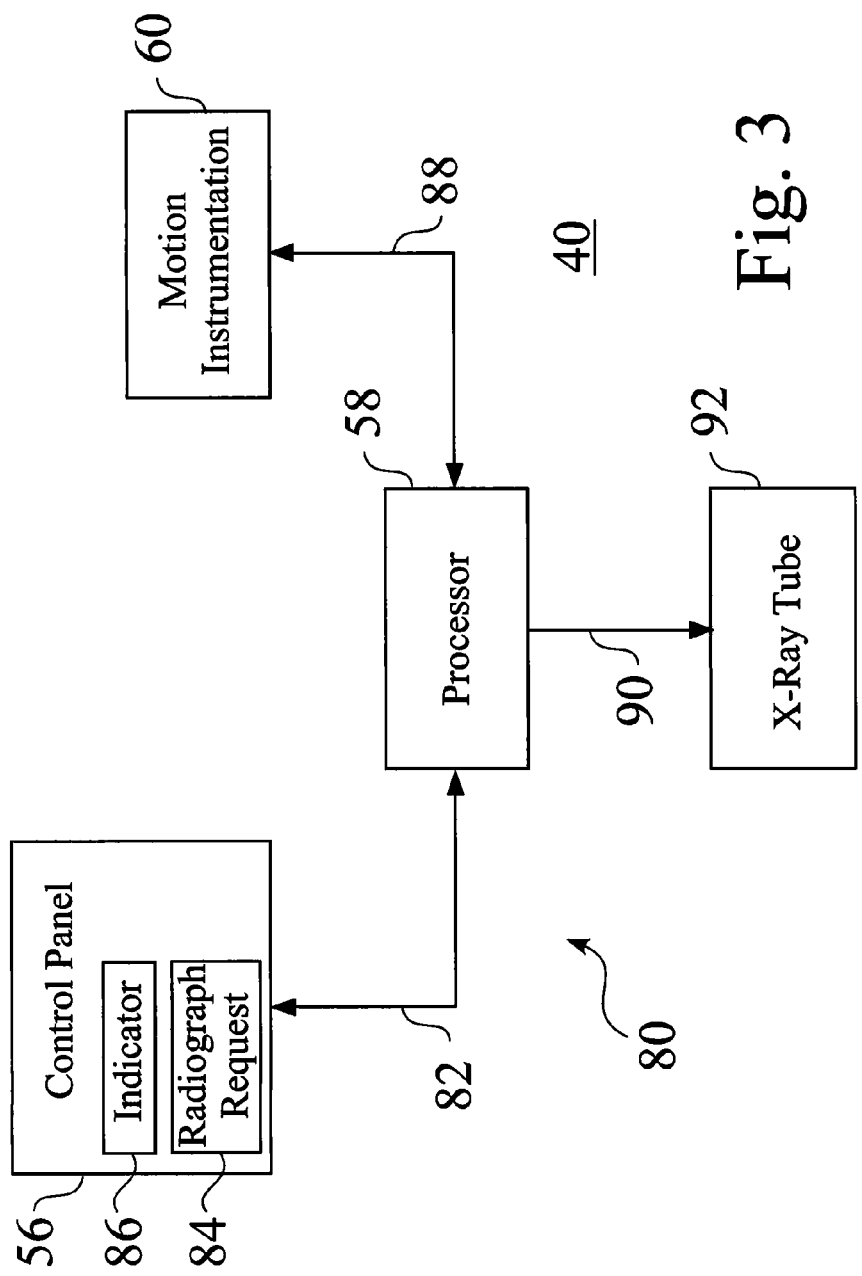
FIG. 3 is a basic block diagram of an exemplary motion-based interlock system for an x-ray machine.
Figure 7:
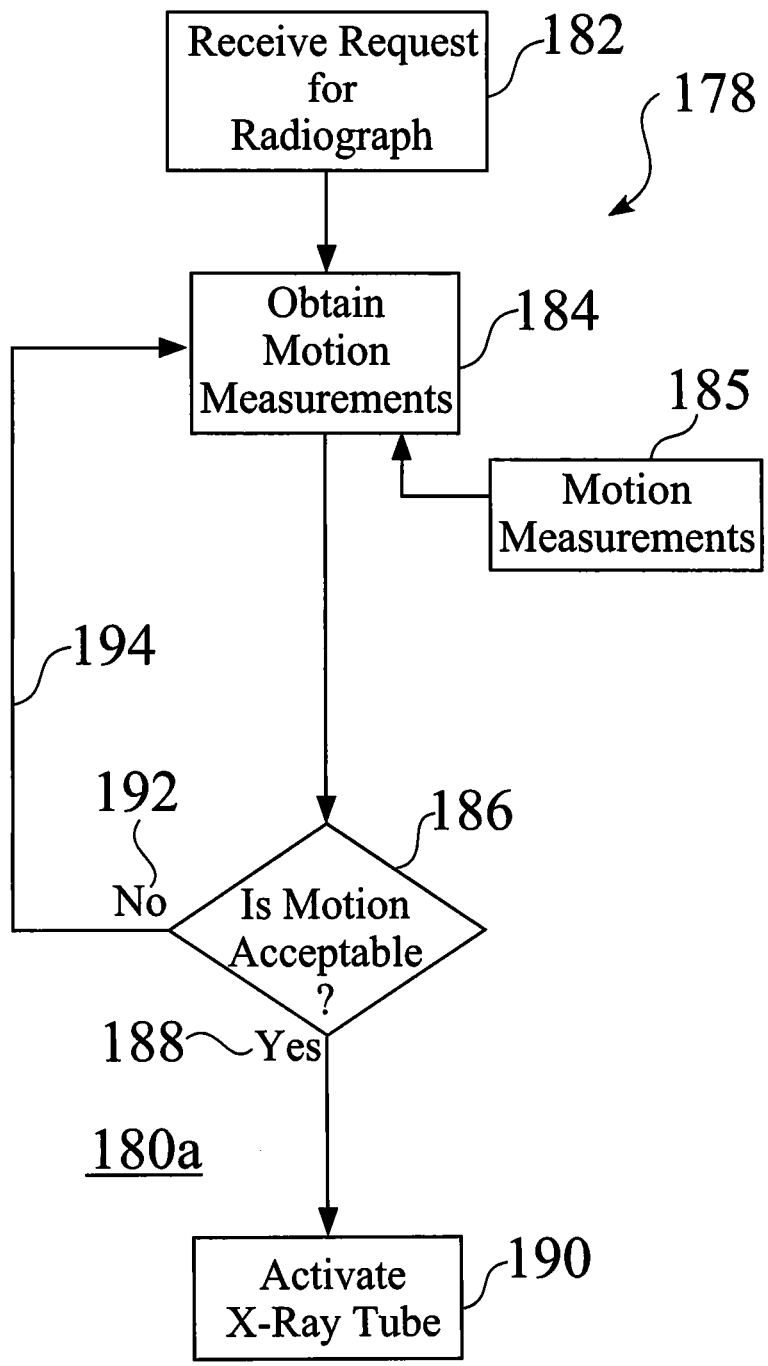
FIG. 7 is a flowchart of an exemplary process associated with a motion-based interlock for an x-ray machine.

FIG. 2 is a schematic view of an exemplary enhanced medical imaging apparatus 44, e.g. a dental x-ray machine 44, having a motion-based interlock system 40. The motion-based interlock system 40 may readily be integrated within a new medical imaging apparatus 44, and/or may be retrofit to an existing medical imaging apparatus 44. The exemplary dental x-ray machine 44 seen in FIG. 2 comprises a base 42, an articulated extension arm 46, and a tubehead 50 housing an x-ray source 92 (FIG. 3). The base 42 anchors the x-ray machine 44 to the floor FLR of dental facility. The exemplary motion-based interlock system 40 seen in FIG. 2 comprises an enhanced control panel 56, with which a dental technician can adjust the radiograph parameters, and initiate image acquisition. The enhanced medical imaging apparatus 44 also typically comprises one or more motion detection mechanisms 60, e.g. 60a-60c, through which one or more motion parameters 185 (FIG. 7) are obtained 184 (FIG. 7).

In some embodiments, the enhanced control panel 56, or a second, auxiliary control panel, may preferably be removed from the base 42, e.g. outside the patient room, allowing the dental technician USR (FIG. 4) to initiate image acquisition from a location with reduced radiation exposure. The articulated extension arm 46 extends outward from the base 42 and supports the tubehead 50, allowing the tubehead 50 to be easily positioned and oriented as needed. The tubehead 50 typically comprises a heavy, e.g. lead, metal housing 52 that encloses the x-ray source 92, such as a hot cathode, i.e. Coolidge, x-ray tube 92.

Figure 4:
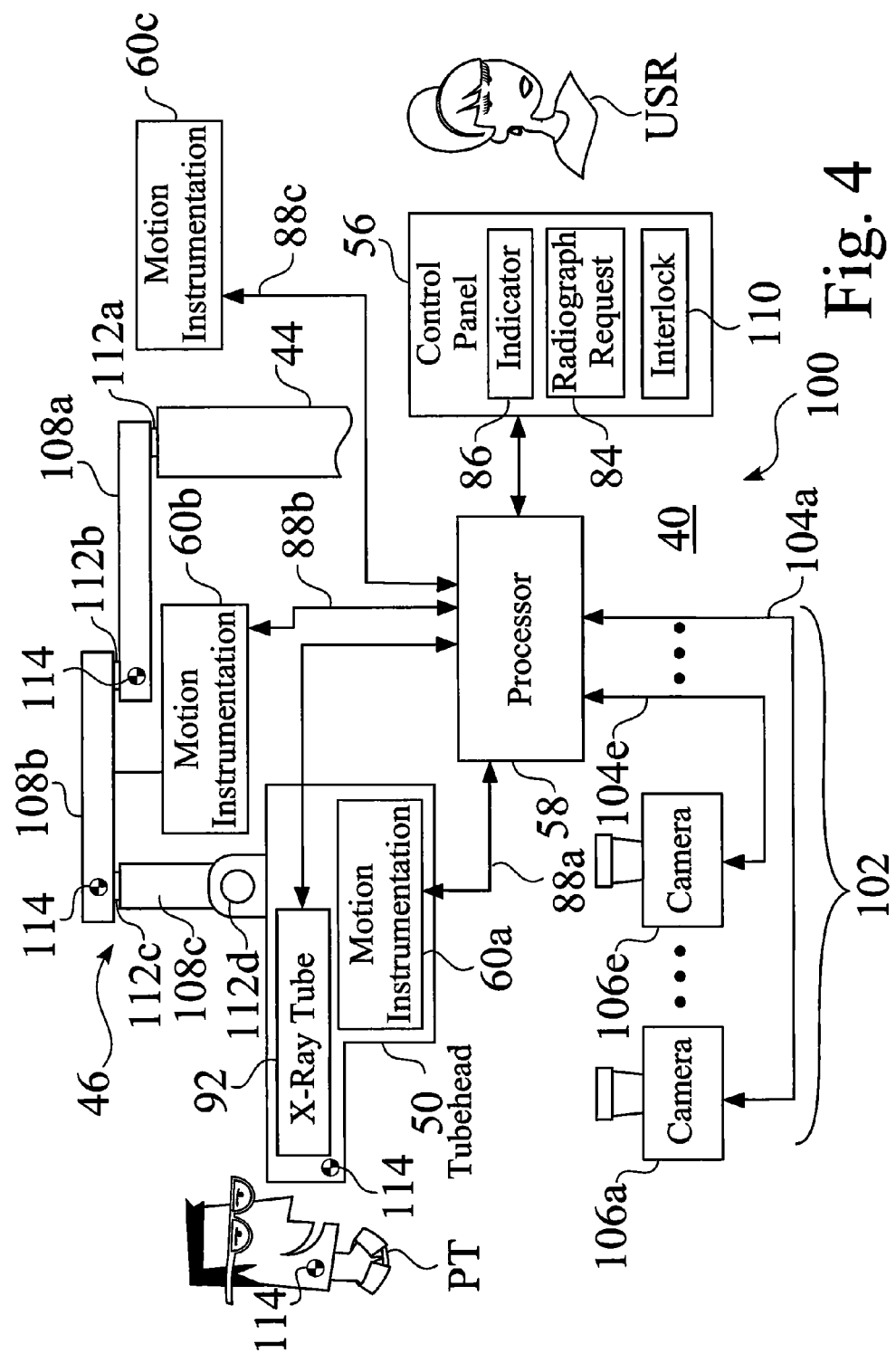
FIG. 4 is a detailed block diagram of an exemplary motion-based interlock system for a medical apparatus.
Figure 5:
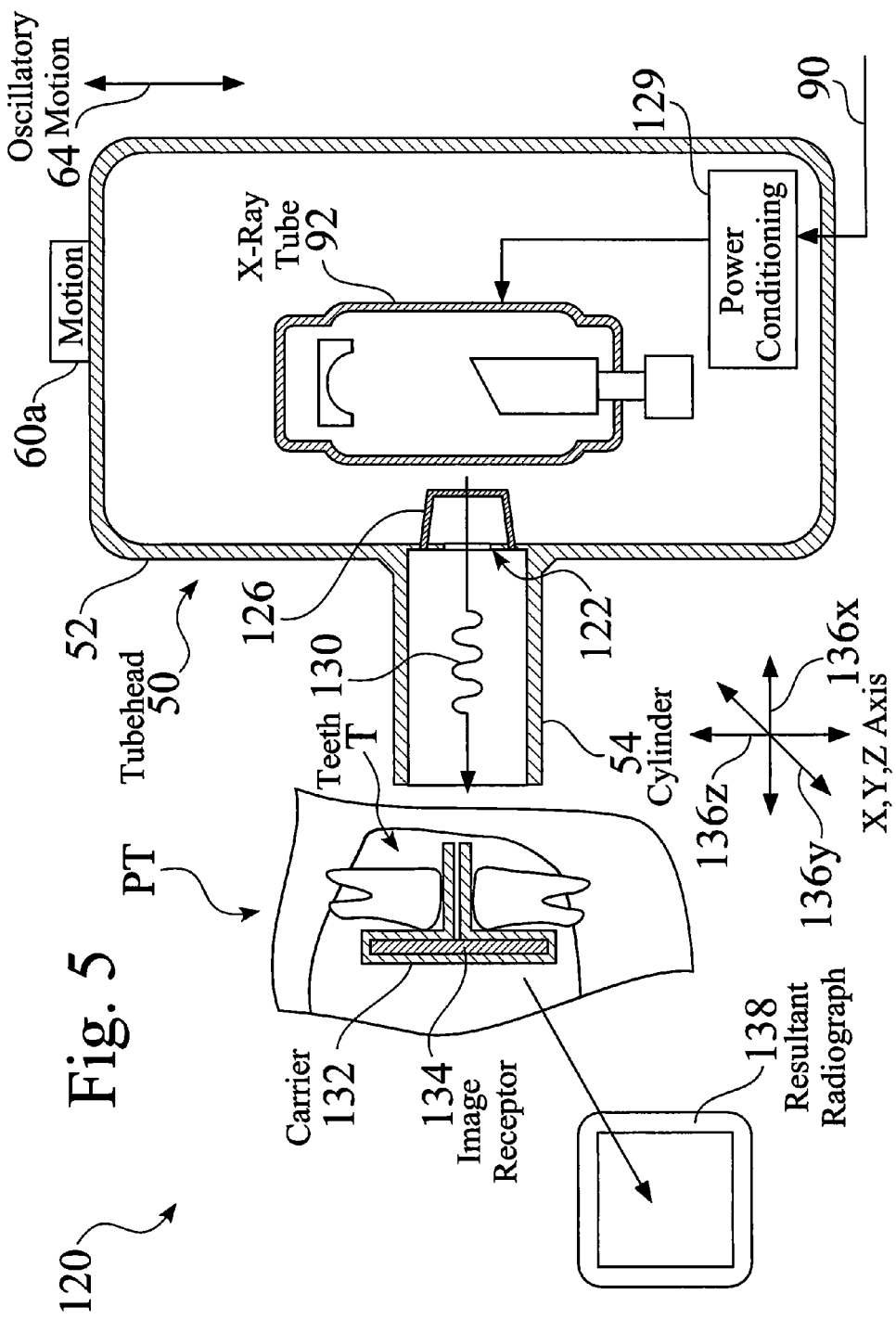
FIG. 5 is a partial cutaway of an exemplary tubehead positioned with respect to a patient.
Figure 8:
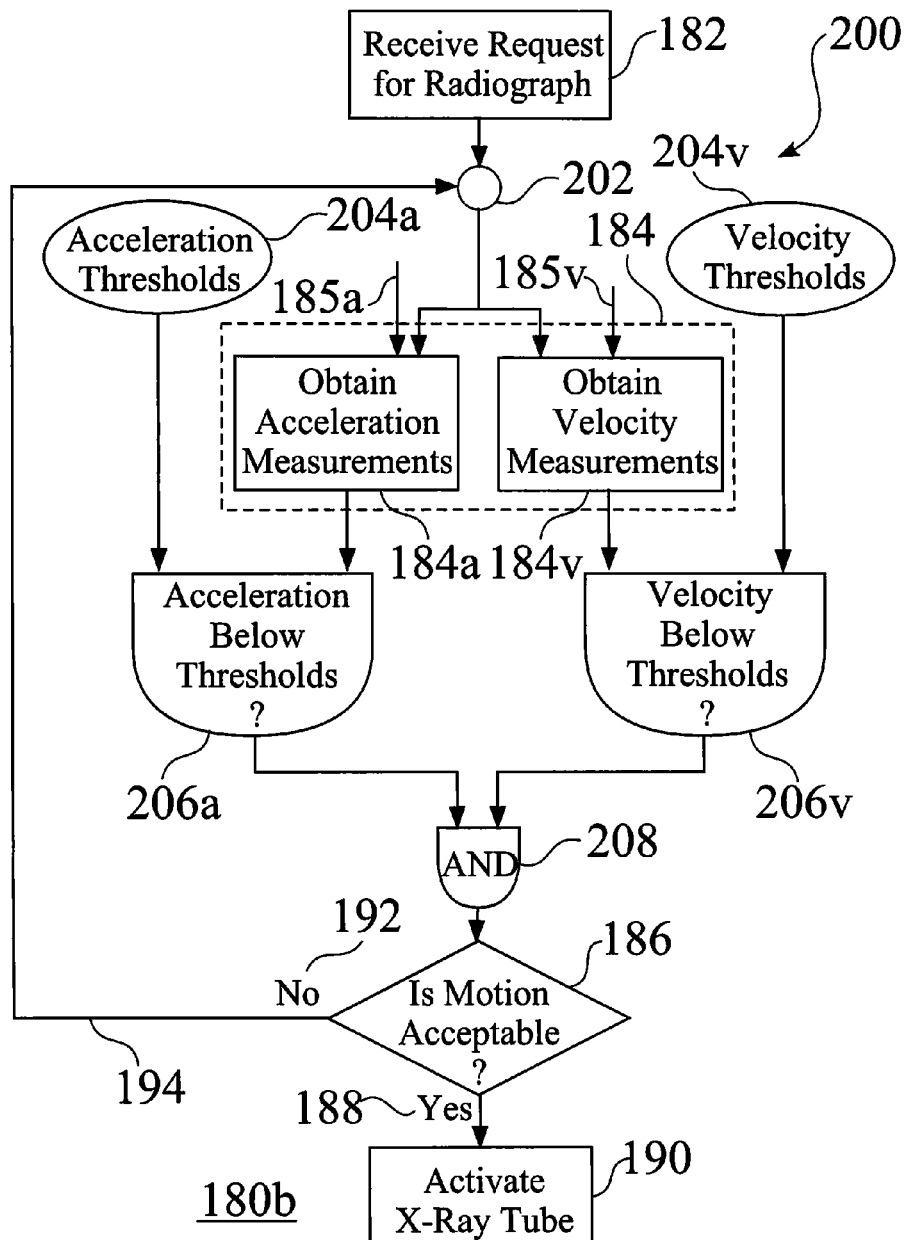
FIG. 8 is detailed flowchart of an alternate exemplary process associated with a motion-based interlock for an x-ray machine.

The motion-based interlock system 40 is configured to prevent the x-ray source 92 from being activated if the current relative motion 64 between the x-ray source 92 and an image receptor 134 (FIG. 5) would compromise the quality of the resulting plain radiograph 138 (FIG. 5). The system 40 may preferably activate an interlock 110 (FIG. 4), based on either or both of the velocity 185v (FIG. 8) and acceleration 185a (FIG. 8) of the tubehead 50, as measured by instrumentation 60, which may preferably be located at any of the tubehead 50, the extension arm 16, or off board the x-ray machine 44. The system 40 may preferably compare the measured motion 185 against one or more acceptable motion thresholds 204 (FIG. 8). If the measured motion 185 exceeds one or more of the acceptable motion thresholds 204, activation 190 (FIGS. 7-9) may preferably be delayed until the motion 64 of the tubehead 50 subsides. By ensuring that the image receptor 134 (FIG. 5) is not exposed while the tubehead 50 is moving substantially, the quality of the resultant radiograph 138 is improved.

Figure 9:
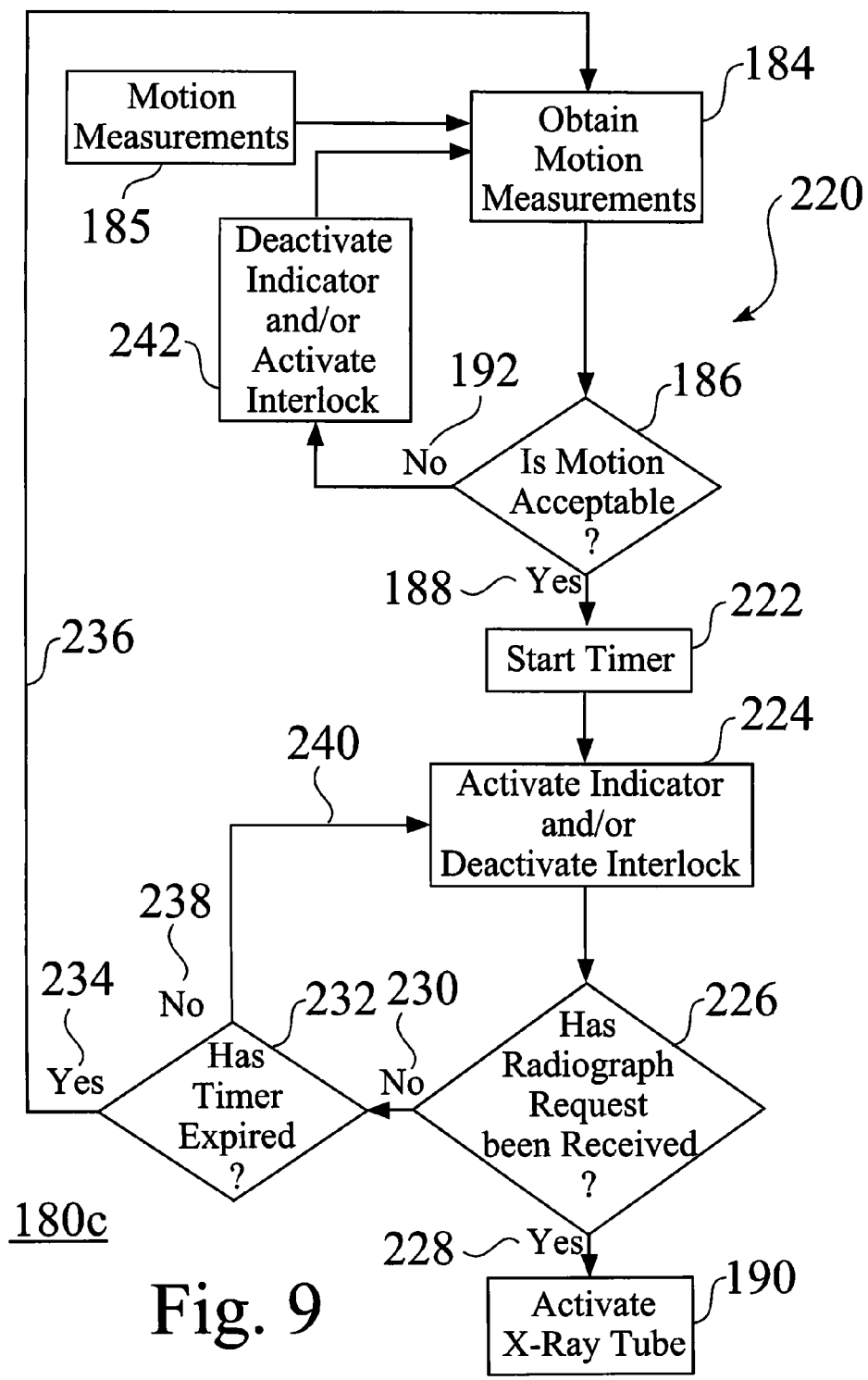
FIG. 9 shows a detailed flowchart of a further exemplary process associated with a motion-based interlock for an x-ray machine.

FIG. 3 is a basic block diagram 80 of an exemplary motion-based interlock system 40 for an enhanced x-ray machine 44. The motion-based interlock system 40 comprises one or more processors 58 that execute one or more embodiments of the motion-based interlock process 180, e.g. 180a (FIG. 7), 180b (FIG. 8), or 180c (FIG. 9). The processor 58 is communicatively coupled 88 with motion instrumentation 60, such as comprising but not limited to any of accelerometers, rotary encoders, or a computer vision system 102 (FIG. 4). For example, the processor 58 may receive any of position information, velocity information, angular velocity information, or acceleration information from one or more instruments 60, such that motion information 185 may be obtained 184, e.g. measured directly, or otherwise determined.

The processor 58 is also communicatively coupled 82 with an enhanced control panel 56 for interacting with the user USR of the system 40. The enhanced control panel 56 may comprise a radiograph request interface 84, such as but not limited to a button 84. The enhanced control panel 56 may preferably comprise one or more indicators 86, such as to indicate whether or not the obtained 184 motion 185 of the tubehead 50 is currently acceptable. The indicators 86 may preferably comprise any of visual indicators 86, audible indicators 86, mechanical indicators 86, or any combination thereof.

In some embodiments of the motion-based radiograph interlock system 40, the indicator 86 may preferably comprise either a multi-colored LED 86, or two single-color LEDs 86, on the control panel 56. For example, the processor 58 may preferably illuminate a multi-colored LED 86 in a green hue to indicate that the current motion 185 is acceptable 188, and a red hue to indicate that the current motion 185 is unacceptable 192. The dental technician USR can thus wait for a green light 86, thereby indicating that the current motion 185 is acceptable 188 (FIG. 7), before initiating image acquisition. This exemplary embodiment has an added benefit of encouraging good habits from the dental technician USR; the dental technician USR can quickly learn that a green light 86 is more rapidly forthcoming if the tubehead 50 is carefully positioned and stabilized prior to exiting the patient room.

Some embodiments 40 of the motion-based radiograph interlock system 40 may preferably comprise any of a mechanical interlock 110, an electrical interlock 110, or an electromechanical interlock 110, e.g. an electromagnetic clutch 110, which prevents the dental technician USR from depressing the button 84 on the control panel 56 that initiates image acquisition. In such an approach, "activating" the indicator 86 corresponds to a release of the interlock 110.

As also seen in FIG. 3 processor 58 is additionally communicatively coupled 90 with the x-ray tube 92, such as through power conditioning circuitry 129 (FIG. 5), e.g. transformer 129, wherein the processor 58 may controllably activate the x-ray tube 92, such as initiated by a technician USR, when the measured motion 185 of the tubehead 50 is determined to be acceptable 186 (FIGS. 7-9).

FIG. 4 is a detailed block diagram of an exemplary motion-based interlock system 40 for a medical apparatus 44, e.g. such as but not limited to a dental x-ray machine 44. As seen in FIG. 4, the processor 58 may preferably be coupled 88 to a wide variety of motion instrumentation 60. For example, the processor 58 may be:

- coupled 88a to motion instrumentation 60a within or attached to the tubehead 50;
- coupled 88b to motion instrumentation 60b within or attached to the articulated extension arm 46; and/or
- coupled 88c to motion instrumentation 60c located off board the x-ray system 44.

In some embodiments of the motion-based interlock system 40, one or more of the motion instruments 60, e.g. 60c, may comprise one or more cameras 106, e.g. 106a-106e, which are 104, e.g. 104a-104e, to the processor 58.

The exemplary articulated extension arm 46 seen in FIG. 4 comprises one or more arm members 108, e.g. 108a-108c, and one or more pivots 112, e.g. 112a-112d, between a base structure 44 and the tubehead 50.

FIG. 5 is a partial cutaway 120 of an exemplary tubehead 50 positioned with respect to a patient PT. The x-rays 130 emitted by the x-ray tube 92 emerge from the metal housing 52 through a lead collimator 122 that partially collimates the x-ray beam 130. A tubehead seal 126, such as comprising a thin aluminum sheet, spans the lead collimator 122, to filter the long wavelength, low energy, i.e. soft, x-rays emitted by the x-ray tube 92 and "harden" the x-ray beam 130. Soft x-rays do not effectively penetrate biological tissues but are instead absorbed. While soft x-rays are not useful for imaging, they remain potentially harmful, and are therefore typically filtered. A position indicating device 54, typically comprising a lead-lined cylinder 54, extends outwards from the metal housing 52, coaxial with the x-ray beam 130, to further collimate the x-ray beam 130 and assist the dental technician USR in aiming the x-ray beam 130.

The exemplary tubehead 50 seen in FIG. 5 is movably mounted to an x-ray imaging apparatus 44 through an articulated extension arm 46, and can be positioned with respect to a patient PT. Movement of the tubehead 50 may be defined with respect to an orthogonal axis system, such as comprising an X-axis 136a, a Y-axis 136y, and a Z-axis 136z. The tubehead 50 may also define random or oscillatory motion 64, such as with respect to one or more axes 136.

Figure 6:
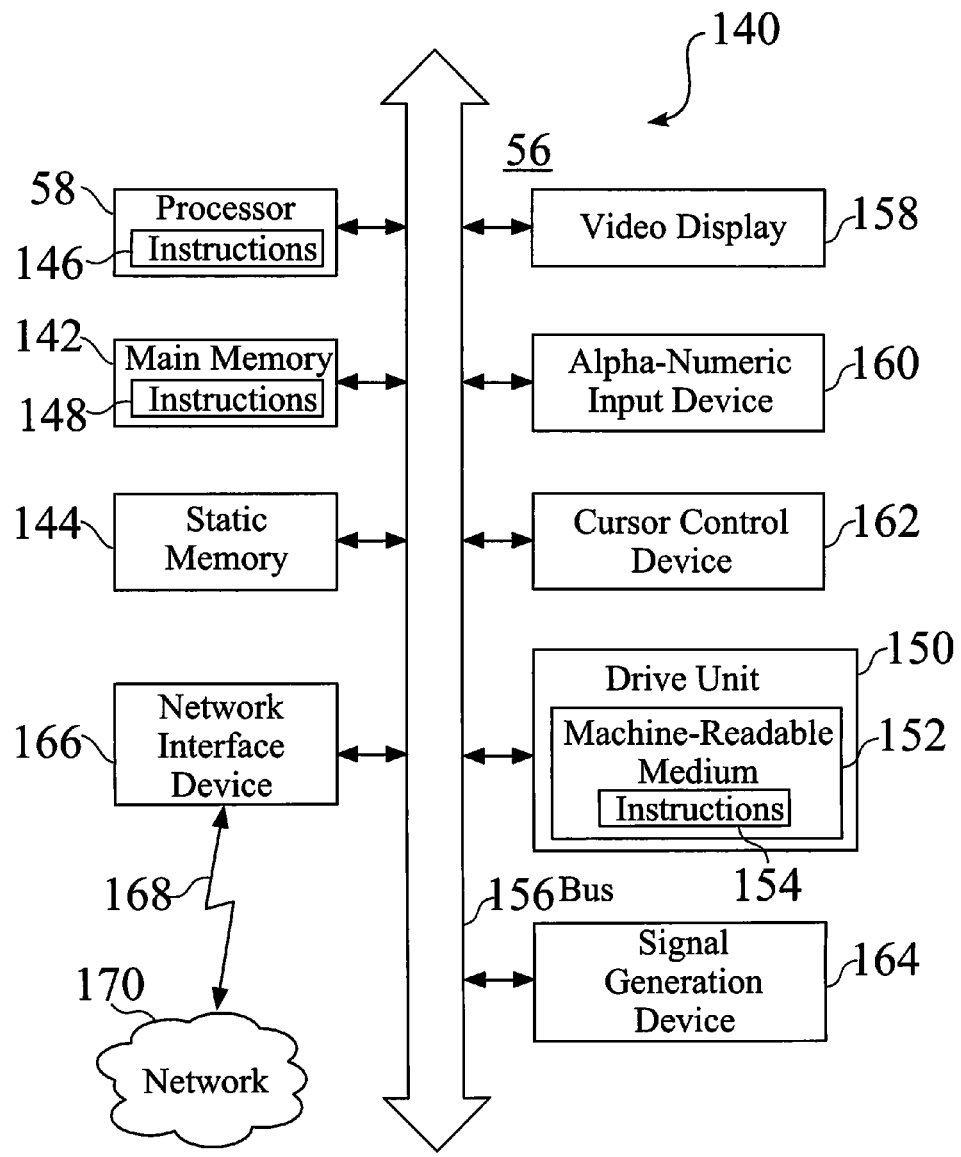
FIG. 6 is a schematic diagram of a machine in the exemplary form of a computer system associated with an enhanced motion-based interlock system.

FIG. 6 is a block schematic diagram of a machine in the exemplary form of a computer system 140 within which a set of instructions may be programmed to cause the machine to execute the logic steps 180 (FIGS. 7-9) of the enhanced motion-interlock system 40.

The exemplary computer system 140 seen in FIG. 6 comprises a processor 58, a main memory 142, and a static memory 144, which communicate with each other via a bus 156. The computer system 140 may further comprise a display unit 158, for example, a light emitting diode (LED) display, a liquid crystal display (LCD) or a cathode ray tube (CRT). The exemplary computer system 140 seen in FIG. 6 also comprises an alphanumeric input device 160, e.g. a keyboard 160, a cursor control device 162, e.g. a mouse, track pad, or touch screen interface 162, a disk drive unit 150, a signal generation device 164, e.g. a speaker, and a network interface device 166.

The disk drive unit 150 seen in FIG. 6 comprises a machine-readable medium 152 on which is stored a set of executable instructions, i.e. software 154, embodying any one, or all, of the methodologies described herein. The software 154 is also shown to reside, completely or at least partially, as instructions 148,146 within the main memory 142 and/or within the processor 58. The software 154 may further be transmitted or received 168 over a network 170 by means of the network interface device 166.

In contrast to the exemplary terminal 140 discussed above, an alternate terminal or to node 140 may preferably comprise logic circuitry instead of computer-executed instructions to implement processing entities. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS (complimentary metal oxide semiconductor), TTL (transistor-transistor logic), VLSI (very large systems integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments may be used as or to support software programs or software modules executed upon some form of processing core, e.g. such as the CPU of a computer, or otherwise implemented or realized upon or within a machine or computer readable medium. A machine-readable medium includes any mechanism for storing or transmitting information in a form readable by a machine, e.g. a computer. For example, a machine readable medium includes read-only memory (ROM); random access memory (RAM); magnetic disk storage media; optical storage media; flash memory devices; electrical, optical, acoustical or other form of propagated signals, for example, carrier waves, infrared signals, digital signals, etc.; or any other type of media suitable for storing or transmitting information.

Further, it is to be understood that embodiments may include performing computations with virtual, i.e. cloud computing. For the purposes of discussion herein, cloud computing may mean executing algorithms on any network that is accessible by internet-enabled devices, servers, or clients and that do not require complex hardware configurations, e.g. requiring cables, and complex software configurations, e.g. requiring a consultant to install. For example, embodiments may provide one or more cloud computing solutions that enable users, e.g. users on the go, to print using dynamic image gamut compression anywhere on such internet-enabled devices, servers, or clients. Furthermore, it should be appreciated that one or more cloud computing embodiments include printing with dynamic image gamut compression using mobile devices, tablets, and the like, as such devices are becoming standard consumer devices.

FIG. 7 shows a flowchart 178 of an exemplary process 180a associated with a motion-based interlock system 40 for an x-ray machine 44 (FIG. 2). The motion-based interlock system 40 is configured to prevent the x-ray source 92 in an x-ray machine 44 from activating 190 if the current motion of the tubehead 50 containing the x-ray source 92 would compromise the quality of the resulting plain radiograph 138 (FIG. 5). At step 182, the processor 58 receives a request 182 for a radiograph 138, e.g. such as through activation of a request control 84 (FIG. 3, FIG. 4) by a technician USR. The processor 58 then obtains 184 one or more motion measurements 185, e.g. 185*a*, 185*v* (FIG. 8), from one or more instruments 60, e.g. such as corresponding to the tubehead 50 and/or the extension arm 46. The processor 58 then determines if the measured motion is acceptable 186. If so 188, the processor 58 activates the x-ray tube 92 to expose the image receptor 134 as requested. If not 192, the processor 58 may return 194 to obtain 184 motion measurements 185, and determine 186 the acceptability of the newly measured motion(s) 185. The processor 58 may preferably wait for a short, predetermined period of time before obtaining 184 one or more subsequent motion measurements 185.

The processor may preferably compare the measured 184 motion 185 against one or more acceptable motion thresholds 204, e.g. 204*a*,204*v* (FIG. 8). If the measured 184 motion 185 exceeds one or more of the acceptable motion thresholds 204, exposure of the image receptor 134 (FIG. 5) is prevented, i.e. interlocked, wherein the process 180*a* returns 194 to repeat steps 184 and 186, until the motion 64 of the tubehead 50 subsides to an acceptable level 188. By ensuring that the image receptor 134 is not exposed while the tubehead 50 is moving 64 substantially, the quality of the resultant radiograph 138 is improved.

FIG. 8 is a detailed flowchart of an alternate exemplary process 180*b* of a motion-based interlock for an enhanced x-ray machine 44. Operation begins when the processor 58 receives a request 182 for a radiograph 138, e.g. such as through activation of a request control interface 84 (FIG. 3, FIG. 4) by a technician USR. For example, the dental technician USR may depress a button 84 on the control panel 56 to begin the image acquisition process 180*b*. The processor 58 then obtains motion measurements 180, e.g. 180*a*, 180*v*, from one or more instruments 60, e.g. such as corresponding to the tubehead 50 and/or the extension arm 46. The processor 58 then determines if the measured motion is acceptable 186. If so, the processor 58 activates the x-ray tube 92 to expose the image receptor 134 as requested. If not 192, the processor 58 may return 194 to obtain 184 motion measurements 185, and determine 186 the acceptability of the newly measured motion 185. The processor 58 may preferably wait for a short, predetermined period of time before obtaining 184 each subsequent motion measurement 185. The processor 58 thus delays activation of the x-ray tube 92, and image acquisition 138, until the motion 64 of the tubehead 50 has subsided to acceptable levels 188.

In some embodiments of the system 40, the processor 58 may preferably obtain 184 one or more acceleration measurements 185*a* and one or more velocity measurements 185*v*. The processor 58 can acquire the measurements 185 from sensors 60 at any of the tubehead 50, at articulated joints 108,112 in the extension arm 46, or off board the x-ray machine 44. In some system embodiments 40, one or more of the motion detection mechanisms 60 may comprise accelerometers, e.g. micro-beam accelerometers, directly coupled to the tubehead 50 to determine the tubehead acceleration along multiple independent, e.g. orthogonal, axes. Alternatively, the processor 58 may acquire multi-axis acceleration measurements using a single multi-axis accelerometer 40. In some system embodiments 40, one or more of the motion detection mechanisms 60 may comprise motion encoders 60, such as but not limited to optical rotary encoders 60, such as to determine the angular velocities of one or segments 108 of the extension arm 46.

FIG. 9 is a flowchart of a further exemplary process 180*c* for a motion-based interlock system 40 associated with an enhanced x-ray machine 44. In the exemplary process 180*c*, the processor 58 indicates to the dental technician USR via the control panel 56 whether or not the current motion 64 of the tubehead 50 has been determined 186 to be acceptable 188. When the motion-based interlock system 40 is activated, e.g. when the x-ray machine 44 enters into a powered state, the processor 58 obtains 184 motion measurements 185. As similarly performed in processes 180*a* and 180*b*, the processor 58 then determines 186 whether or not the measured 184 motion 185 is acceptable 188. If the motion 185 is not acceptable 192, the processor 58 activates 242 the interlock 110 and/or deactivates 242 the control panel indicator 86, if active, and obtains 184 further motion measurements 185. If the motion 185 is acceptable 188, the processor 58 starts a timer 222, and activates 224 the control panel indicator 86 and/or deactivates 242 the interlock 110. If the processor 58 has received a request 228 for a radiograph 138, the processor 58 activates 190 the x-ray tube 92, to expose the image receptor 134 as requested. Otherwise 230, the processor 58 determines 232 whether the timer has expired, i.e. exceeded a predetermined threshold. If the timer has not expired 238, the processor 58 returns 240 and either activates 224 or maintains the active state of the indicator 86, and again checks 226 if a request for a radiograph 138 has been received 228. If the timer has expired 234, the processor 58 returns 236 and obtains 184 further motion measurements 185.

Figure 10:
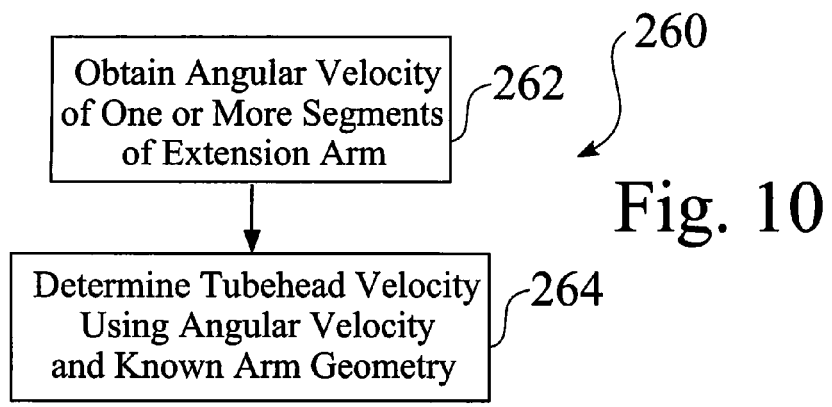
FIG. 10 shows an exemplary process for determining tubehead velocity using the angular velocity of one or more segments of an extension arm, and the known geometry of the extension arm.

FIG. 10 shows an exemplary process 260 for determining tubehead velocity 264 using 262 the angular velocity measurements 185 of one or more segments 108, e.g. 108*a*-108*c* (FIG. 4) of an extension arm 46, and the known geometry of the extension arm 46. The known geometry of the extension arm allows the processor 58 to determine the tubehead velocity 185*v*, relative to the assumed stationary base 42, from the angular velocities 185 of the segments 108.

Figure 11:
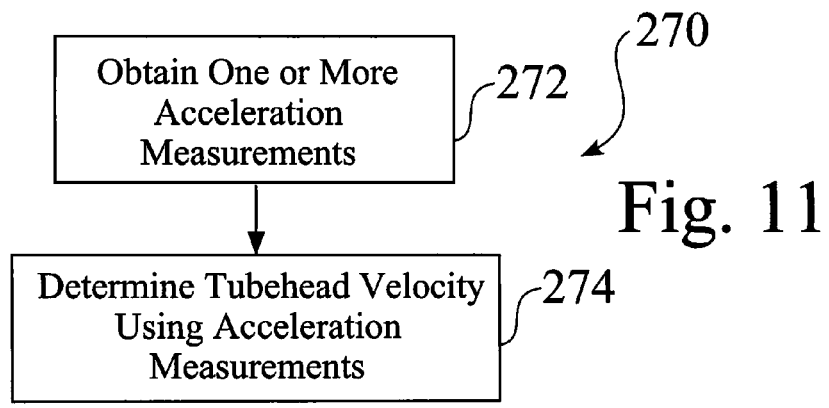
FIG. 11 shows an exemplary process for determining tubehead velocity using one or more acceleration measurements.

FIG. 11 shows an exemplary process 270 for determining 274 tubehead velocity 185*v* using 272 one or more acceleration measurements 185*a*. For example, the processor 58 may preferably be configured to compute tubehead velocity 185*v* from the acceleration measurements 185*a*, via integration.

Figure 12:
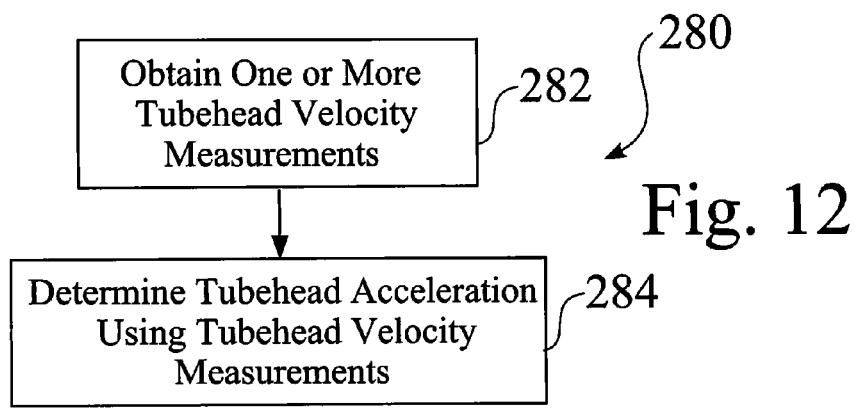
FIG. 12 shows an exemplary process for determining tubehead acceleration using one or more tubehead velocity measurements.

FIG. 12 shows an exemplary process 280 for determining 284 tubehead acceleration 185*a* using 282 one or more tubehead velocity measurements 185*v*. For example, the processor 58 may preferably be configured to compute 284 tubehead acceleration 185*a* from the tubehead velocity measurements 185*v*, via differentiation.

In some embodiments of motion-based interlock systems 40 and associated processes 108, the potentially redundant nature of such motion measurements 185 may preferably be used by the processor 58 to refine the accuracy of one or more measurements 185.

As seen in FIG. 2 and FIG. 4, the motion-based interlock system 40 may preferably obtain 184 motion measurements 185 of the tubehead 50 using sensors 60*c* off board the x-ray machine 44. In some embodiments of the motion-based interlock system 40, one or more off-board sensors 60*c* may be located at or otherwise correspond to any of the image receptor 134, the carrier 132, the patient PT, or any combination thereof, wherein obtained 184 measurements 185 from the off-board sensors 60*c* may preferably be combined with measurements 185 from any the tubehead 50 and/or the articulated extension arm 86, wherein the relative motion between the tubehead 50 and the image receptor 134 is accurately determined.

In some embodiments of the motion-based interlock system 40, a computer vision system 102, comprising one or more cameras 104, e.g. 104*a*-104*e*, may preferably be positioned within the patient room, to track the motion 185 of the tubehead 50, the articulated extension arm 46, the image receptor 134, the carrier 132, the patient PT, or any combination thereof. The computer vision system 102 may preferably comprise a plurality of cameras 104, e.g. a stereo vision system 102, such as to resolve potential motion degeneracies along the optical axis of a single camera 104.

Optionally, the tubehead 50 and/or other target, can be fitted with active or passive fiducials 114 (FIG. 4), i.e. markers, such as but not limited to infrared light emitting diode (IR LED) beacons, to simplify and improve the accuracy of tracking one or more targets, e.g. comprising the tubehead 50, the articulated extension arm, the image receptor 134, the carrier 132, the patient PT, or any combination thereof, within the captured camera imagery. The processor 58 can therefore determine the acceleration 185a and velocity 185v of the tubehead 50, directly from observed spatial trajectory of the tubehead 50. The processor 58 may also determine the acceleration 185a and velocity 185v of the image receptor 134, such as to determine the relative motion between the x-ray source 92 and the image receptor 134.

In some embodiments of the motion-based interlock process 180, once the processor 58 determines the acceleration 185a and velocity 185v of the tubehead 56, the motion parameters 185a,185v are compared with predetermined acceleration and velocity thresholds 204a,204v. The processor 58 may preferably reference distinct acceleration and velocity thresholds 204a,204v for each of the spatial axes 136 along which the tubehead 50 may move. For example, lower thresholds 204 may be used for those axes 136 along which motion 185 is particularly harmful to the resulting quality of the radiograph 138, e.g. axes 136 largely transverse to the axis of the x-ray beam 130. Since the motion 185 of the tubehead 50 is typically oscillatory 64 in nature, with acceleration 185a and velocity 185v periodically attaining near-zero values in an out-of-phase fashion, the processor 58 may preferably require that both the acceleration 185a and velocity 185v of the tubehead 50 be below their predetermined thresholds 204a and 204v.

If so, the motion 185 of the tubehead 50 is determined 186 to be acceptable 188, wherein the processor 58 may proceed with either:
  activation 190 to the x-ray tube 92 to expose the image receptor 134; or
  illuminating an indicator 86, optionally releasing a hard interlock 110, and accepting a request 182 from a user USR to activate 190 the x-ray tube 92.

If not 192, the processor 58 may obtain 184 further motion measurements 185, and proceed to determine 186 the acceptability of the newly measured motion(s) 185.

Alternatively, the processor 58 may use either only the acceleration measurements 185a, or only the velocity measurements 185v, and compare a recent history of measurements to the predetermined thresholds, wherein the recent history may be stored in a buffer or other storage, e.g. 142 (FIG. 6). For example, the processor 58 may preferably use an exponentially decaying weighted average of recent tubehead accelerations 185a or velocities 185v, with a decay constant as long or longer than the characteristic oscillatory period of the extension arm 46.

While exemplary embodiments are disclosed herein in association with an x-ray machine 44 for medical or dental applications, the motion-based radiograph interlock system 40 and process 180 may alternately be configured for a wide variety of alternate applications, such as but not limited any of industrial x-ray systems, trans-IR imaging systems, other imaging systems, or magneto-resonance (MRI) chambers.

As well, while exemplary embodiments are disclosed herein in association with measured motion parameters of the tubehead and/or one or more portions of an articulated extension arm, the motion-based radiograph interlock system 40 and process 180 may alternately be configured to obtain motion parameters of any portion of an imaging apparatus, and may preferably obtain motion parameters of any of the image receptor or the subject, such as to consider relative motion between the tubehead and a target.

Accordingly, although the invention has been described in detail with reference to a particular preferred embodiment, persons possessing ordinary skill in the art to which this invention pertains will appreciate that various modifications and enhancements may be made without departing from the spirit and scope of the claims that follow.

The invention claimed is:

1. A process associated with a radiograph structure having an imaging device, comprising the steps of:
  obtaining at least one motion parameter associated with the radiograph structure;
  determining if the obtained at least one motion parameter associated with the radiograph structure has an acceptable value that falls below at least one of preset acceleration or velocity thresholds;
  wherein said at least one motion parameter comprises at least one of:
    tubehead velocity determined using angular velocity measurements of one or more extension arm segments and the known geometry of the extension arm;
    tubehead velocity determined using one or more acceleration measurements; or
    tubehead velocity determined using one or more velocity measurements;
  upon determining that the at least one motion parameter has an acceptable value, automatically activating the imaging device to acquire the radiograph image based upon the determination step;
  upon determining that the at least one motion parameter does not have an acceptable value, automatically preventing activation of the imaging device; and
  visually, audibly, or mechanically indicating whether the obtained at least one motion parameter has an acceptable value.

2. The process of claim 1, wherein the imaging device comprises an x-ray tube.

3. The process of claim 1, wherein the step of automatically preventing activation of the imaging device comprises activating any of a mechanical interlock, an electrical interlock, or an electromechanical interlock.

4. The process of claim 1, wherein the radiograph structure has a patient corresponding therewith, an image receptor for placement with respect to the patient, and a carrier associated with the image receptor, wherein the process further comprises the step of:
  obtaining at least one additional motion parameter associated with any of the patient, the image receptor, or the carrier;
  wherein the determination step is further based on the obtained additional motion parameter.

5. The process of claim 1, wherein the acceptable value comprises a threshold value.

6. The process of claim 5, wherein the threshold value is stored in a memory.

7. The process of claim 1, further comprising the step of:
  starting a time period if the obtained at least one motion parameter has an acceptable value;
  activating an output during the time period, wherein the activated output is indicative of the acceptable state; and allowing user activation of the imaging device during the duration of the time period.

8. The process of claim 1, wherein the at least one motion parameter is obtained from any of an accelerometer, a rotary encoder, or a computer vision system.

9. The process of claim 1, wherein the obtained motion parameter is based on any of a measured motion parameter or a determined motion parameter.

10. The process of claim 1, further comprising the steps of:
comparing the at least one motion parameter against one or more acceptable motion thresholds; and
delaying the activation of the imaging device until the motion of the imaging device subsides if the measured motion exceeds one or more of the acceptable motion thresholds.

11. A system associated with a radiograph structure having an imaging device associated therewith, comprising:
a mechanism of obtaining motion measurements corresponding to at least one portion of the radiograph structure;
at least one processor in communication with the imaging device and the mechanism, wherein the at least one processor is configured to
obtain at least one motion measurement from the mechanism,
determine if the obtained motion measurement has an acceptable value that falls below at least one of preset acceleration or velocity thresholds, and either
automatically activate the imaging device to acquire a radiograph image if the obtained motion measurement has an acceptable value, or
automatically prevent activation of the imaging device if the obtained motion measurement has an unacceptable value;
wherein said at least one motion parameter comprises at least one of:
tubehead velocity determined using angular velocity measurements of one or more extension arm segments and the known geometry of the extension arm;
tubehead velocity determined using one or more acceleration measurements; or
tubehead velocity determined using one or more velocity measurements; and
an indicator configured to visually, audibly, or mechanically indicate whether the obtained at least one motion parameter has an acceptable value.

12. The system of claim 11, wherein the imaging device comprises an x-ray tube.

13. The system of claim 11, further comprising an interlock, wherein the processor is configured to activate the interlock to prevent the activation of the imaging device if the obtained motion measurement has an acceptable value.

14. The system of claim 11, wherein the radiograph structure comprises a base, a tubehead, and an articulated extension arm that extends from the base to the tubehead, wherein the imaging device is located within the tubehead, and wherein the at least one motion measurement corresponds to motion of any of the tubehead or the articulated extension arm.

15. The system of claim 14, wherein the at least one motion measurement corresponds to any of velocity or acceleration.

16. The system of claim 11, further comprising a memory, wherein the threshold value is stored in the memory.

17. The system of claim 11, wherein the processor is further configured to
start a time period if the obtained motion measurement has an acceptable value,
activate an output during the time period, wherein the activated output is indicative of the acceptable state, and
allow user activation of the imaging device during the duration of the time period.

18. The system of claim 11, wherein the mechanism of obtaining motion measurements comprises any of an accelerometer, a rotary encoder, or a computer vision system.

19. The system of claim 11, wherein the obtained motion parameter is based on any of a measured motion parameter or a determined motion parameter.

20. The system of claim 11, wherein the processor is further configured to
compare the at least one motion parameter against one or more acceptable motion thresholds, and
delaying the activation of the imaging device until the motion of the imaging device subsides if the measured motion exceeds one or more of the acceptable motion thresholds.

21. An apparatus associated with a radiograph system having an imaging device associated therewith, comprising:
a mechanism that is configured to obtain motion parameters corresponding to at least one portion of the radiograph system;
at least one processor in communication with the imaging device and the mechanism that is configured to obtain the motion parameters, wherein the at least one processor is configured to
obtain at least one motion parameter from the mechanism that is configured to obtain the motion parameters, and
determine if the obtained motion parameter has an acceptable value that falls below at least one of preset acceleration or velocity thresholds,
wherein said at least one motion parameter comprises at least one of:
tubehead velocity determined using angular velocity measurements of one or more extension arm segments and the known geometry of the extension arm;
tubehead velocity determined using one or more acceleration measurements; or
tubehead velocity determined using one or more velocity measurements;
wherein when the processor determines that the obtained motion parameter has an acceptable value, the processor is configured to
automatically proceed with any of activation of the imaging device or
deactivate an interlock to allow activation of the imaging device by a user; and
wherein when the processor determines that the obtained motion parameter does not have an acceptable value, the processor is configured to
automatically proceed with any of preventing activation of the imaging device or activate the interlock to prevent activation of the imaging device by a user; and
an indicator configured to visually, audibly, or mechanically indicate whether the obtained at least one motion parameter has an acceptable value.

22. The apparatus of claim 21, wherein the mechanism that is configured to obtain the motion parameters comprises any of a sensor or a camera.

23. The apparatus of claim 21, further comprising:
a control panel in communication with the processor.

24. The apparatus of claim 23, wherein the control panel comprises any of a radiograph request input control, or an indicator for displaying if the processor has determined that the obtained motion measurement has an acceptable value.

25. The apparatus of claim 21, wherein the processor is further configured to calculate a second motion parameter based upon the obtained motion parameter.

* * * * *